(12) United States Patent
Matsukawa et al.

(10) Patent No.: US 7,113,816 B2
(45) Date of Patent: Sep. 26, 2006

(54) **ULTRA-MINIATURE *IN-VIVO* ELECTRODE USED FOR MEASURING BIOELECTRICAL NEURAL ACTIVITY**

(75) Inventors: Kanji Matsukawa, Hiroshima (JP); Takako Ito, Toyonaka (JP); Kazuhiko Kondoh, Takarazuka (JP); Yasuo Seki, Takarazuka (JP)

(73) Assignee: Nippon Cable System Inc., (JP)

( * ) Notice: Subject to any disclaimer, the term of this patent is extended or adjusted under 35 U.S.C. 154(b) by 0 days.

(21) Appl. No.: 10/431,508

(22) Filed: May 8, 2003

(65) Prior Publication Data

US 2004/0006281 A1   Jan. 8, 2004

(30) Foreign Application Priority Data

Jun. 18, 2002   (JP) .............................. 2002-176883

(51) Int. Cl.
*A61B 5/04* (2006.01)

(52) U.S. Cl. ........................ 600/377; 600/393; 607/118

(58) Field of Classification Search ................ 600/377, 600/393; 607/118
See application file for complete search history.

(56) References Cited

U.S. PATENT DOCUMENTS

| | | | |
|---|---|---|---|
| 3,157,181 A * | 11/1964 | McCarty | 607/118 |
| 3,957,036 A * | 5/1976 | Normann | 600/377 |
| 4,628,942 A * | 12/1986 | Sweeney et al. | 607/118 |
| 4,649,936 A * | 3/1987 | Ungar et al. | 607/118 |
| 4,750,499 A * | 6/1988 | Hoffer | 607/116 |
| 4,774,967 A * | 10/1988 | Zanakis et al. | 607/118 |
| 4,940,065 A * | 7/1990 | Tanagho et al. | 607/118 |
| 5,324,322 A * | 6/1994 | Grill et al. | 607/118 |
| 5,487,756 A * | 1/1996 | Kallesoe et al. | 607/118 |
| 5,741,319 A * | 4/1998 | Woloszko et al. | 607/118 |
| 5,938,596 A * | 8/1999 | Woloszko et al. | 600/377 |
| 2003/0045909 A1* | 3/2003 | Gross et al. | 607/9 |
| 2003/0050677 A1* | 3/2003 | Gross et al. | 607/72 |

FOREIGN PATENT DOCUMENTS

JP      2001-157669 A1     6/2001
WO      WO9117791      * 11/1991

* cited by examiner

*Primary Examiner*—Lee S. Cohen
(74) *Attorney, Agent, or Firm*—Rader, Fishman & Grauer PLLC

(57) ABSTRACT

An ultra-miniature in-vivo electrode used for measuring the bioelectrical neural activity etc. in a living body with small cubic volume, slight burden to the living body, and high insulation performance, thereby facilitating long term stable measurements. Structurally the in-vivo electrode comprises conductors 13, 14 made of polymeric material having a through-hole 19 in each center so as to lead a measuring object 18; a intervening member 15 made of non-conductive polymeric material provided in between the conductors so as to insulate the periphery of the conductors; edge members 16, 17 provided in the outer edge of the conductors; a clad body 12 made of cylindrical insulant enclosing the periphery of them; measuring wires 21,22 to lead electricity to outside from each conductor 21, 22; a slit 26 which reaches the through-hole 19 from the outside surface being formed in all of the conductors, the intervening member, the edge members, and the clad body.

8 Claims, 8 Drawing Sheets

(a) 
(b) 
(c)

(a)

(b)

(a)

(b)

(c)

ULTRA-MINIATURE IN-VIVO ELECTRODE USED FOR MEASURING BIOELECTRICAL NEURAL ACTIVITY

FIELD OF THE ART

This invention generally relates to an ultra-miniature in-vivo electrode or a microelectrode for measuring the minimal bioelectric potential difference or minimal current of nerve fascicles, and particularly to an ultra-miniature in-vivo electrode usable under the embedded condition in a living body with only a slight burden to the living body, thereby facilitating long-term continuous measurements of bioelectrical neutral activity.

BACKGROUND ART

In conventional measurements of the neural activity of a living body, electrodes using such materials as biomolecular collagen and metallic silver wires are contacted to a nerve fascicle, and the measurement of a minimal current flow in the nerve fascicle is performed through insulated wires affixed to the electrode. These electrodes are used for the measurements of neural activities including peripheral nerves having the diameter of the order of millimeters, and sympathetic nerves to the heart and kidney having the diameter of the order of several hundreds micrometers. However, the sympathetic nerves to the other visceral organs such as the adrenal, splenic, and digestive organs etc. or the nerves distributing to skeletal muscles, skin, and brain/spinal chord have extremely smaller diameters on the order of less than 100 µm, and they are vulnerable to mechanical damages. Furthermore, it is difficult to maintain good insulation performance in the living body for longer than about one week, for which conventional measurements can be achieved. Finally, low signal levels of some microvolts measured in the small nerve bundle cause difficulties in achieving reliable signal processing.

As for an in-vivo electrode, which may enhance the reliability of signal processing, a microelectrode is disclosed by Japanese Unexamined Patent Publication No. 157669/2000. The microelectrode has characteristic as shown in FIGS. 10a~c and a signal processing electrical circuit assembled in the vicinity of the microelectrode. The patent application discloses a crank like electrode 101 having a horseshoe shape into which a neural axon bundle 100 is led in between with contiguity. Further in the application, a furcated electrode (See FIG. 10b-102) and a needle like electrode (See FIG. 10c-103) stabbing the neural bundle 100 are disclosed respectively.

Any of the crank like, furcated, and needle like microelectrodes described above can be applied only to a thick nerve bundle and has limits in stable measurements of neural activity. Further, the measuring object is a microscopic-level nerve fascicle in the living body; which can easily be mechanically damaged or killed. Furthermore, it is difficult to maintain good insulation performance of an implantable electrode for a long period of time and to keep it stably fitted to the thin nerve fascicle. Especially for the purpose of elucidating the neural regulation of the cardiovascular system, which is controlled by the brain and autonomic nerve system, it is necessary to simultaneously measure multiple autonomic nerve activities, which governs the above-described visceral organs. This invention is directed to provide an ultra-miniature in-vivo electrode, which facilitates multidimensional measurements without any damage to a thin nerve bundle. Moreover, this invention is directed to provide an ultra-miniature in-vivo electrode, which has high insulation performance facilitating long-term stable measurements.

DISCLOSURE OF INVENTION

An ultra-miniature in-vivo electrode of this invention, used for measuring the bioelectrical neural activity, comprises, a pair of conductor made of polymeric material having a through-hole in each center so as to lead a measuring object; and an insulator made of polymeric material which insulates the periphery of the conductors and supports each conductor; wherein the through-holes are aligned with each other in a straight line at an interval; and a pair of wires connected to each conductor and penetrating the insulator to its outside where the surface of the wires are insulated.

In another aspect of the above-mentioned in-vivo electrode, the conductor and the insulator are made of elastic body like rubber, and the conductor and the insulator as a whole have a slit which reaches the through-hole from the outside surface, in order to guide the measuring object into the through-hole. Further, this slit may always be closed by elastic force.

In another aspect of the above-mentioned in-vivo electrode further comprises a thread binding periphery of the insulator so as to keep the slit closed.

In another aspect of the above-mentioned in-vivo electrode further comprises, an earth electrode laid on the surface of the insulator and an earth wire connected to the earth electrode, wherein the surface of the wire is insulated.

In another aspect of the above-mentioned in-vivo electrode, the insulator comprises an intervening member provided in between the conductor, an edge member covering each edge of the conductors, and a cylindrical member enclosing the whole periphery of the conductors, the intervening member, and the edge member.

In this in-vivo electrode, the periphery of the separated portion of the measuring object can be enclosed with a pair of electric conductors by leading a measuring object into the through-hole of the electric conductors. Because wires are connected to each electric conductor, the electrical potential difference between the separated portions of the measuring object can be measured easily by observing the electric potential difference between the other ends of the wires. Further, since the electric conductor encloses the whole periphery of the measuring object, better contact to the measuring object can be stably maintained compared with the conventional crank like, furcated, and needle like electrode, thereby enabling stable setting to thin peripheral nerves etc. The use of polymeric material enables molding of thin, short electrodes, which enables a number of settings and the continuation of multidimensional measurements without any damage against a thin nerve bund. Since the electric conductor is insulated by the surrounded insulator and the wires exposed to the outside area are also insulated, the measurement can be performed by embedding the electrode into a living body, thereby enabling a long term stable continuous measurement.

In the in-vivo electrode in which the conductors and the insulator are made of an elastic body like rubber, respectively, and a slit which reaches the through-hole from the outside surface, is formed in order to guide the measuring object into the through-hole wherein the slit is always closed by elastic force, the through-hole is exposed outside when the slit is opened with the use of elasticity. Therefore, the measuring objects such as neural fascicles can easily be led into the through-hole. When the force expanding the slit is loosened, the slit closes naturally to enclose the measuring object by its elasity. Accordingly, setting and removing of measuring objects such as a thin nerve is easily performed. That is to say, this in-vivo electrode not only enables a continuously stable setting to the measuring object but also allows for ease in setting and removal of the measuring object.

An in-vivo electrode, which is provided with a thread binding the periphery of the insulator so as to keep the slit closed, binds the periphery of the insulator using a textile thread, which makes the contact of the slit tight thereby reducing the possibility of insulation breakdown due to infiltration of body fluid etc. through the slit.

The in-vivo electrode provided with an earth electrode laid on the surface of the insulator and with the earth wire having an insulated surface and connected to the earth electrode, so as to embed the whole body into a living body, allows the end of the earth wire to be electrically and stably connected to the living body. It saves the labor of having to connect an earth wire separately to the living body for a reference of the electrical potential and also saves the labor of having to remove the wire. Further, it allows the earth wire to be lead out of the living body together with the wires connected to the conductors.

In the in-vivo electrode which is provided with the insulator being composed of an intervening member in between the conductor, an edge member covering each edge of the conductors, and a cylindrical member enclosing whole periphery of the conductors, the intervening member, and the edge members, easy assembling is accomplished by shoving in one piece of the conductor, the intervening member, and the other piece of the conductor from one end of the cylindrical member and then fitting the edge members.

BEST MODE FOR CARRYING OUT THE INVENTION

The best mode for carrying out of the invention is described with reference to accompanying drawings in which.

Figure 7:
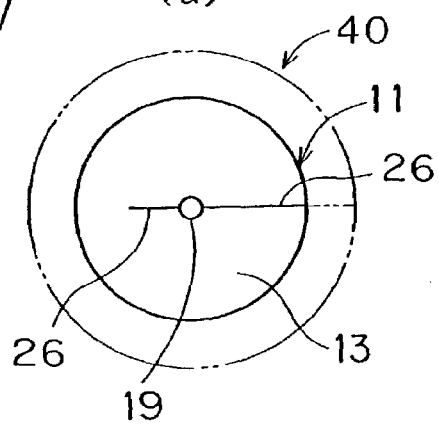
Figure 7:
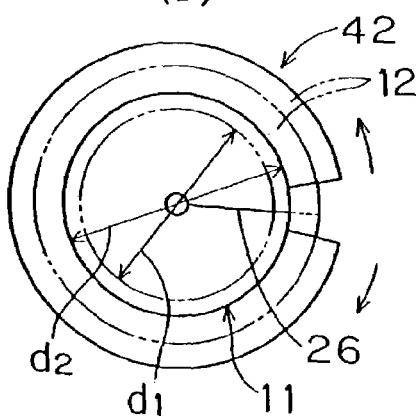
Figure 7:
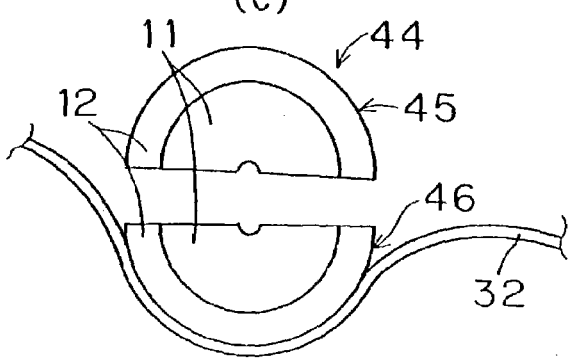
Figure 8:
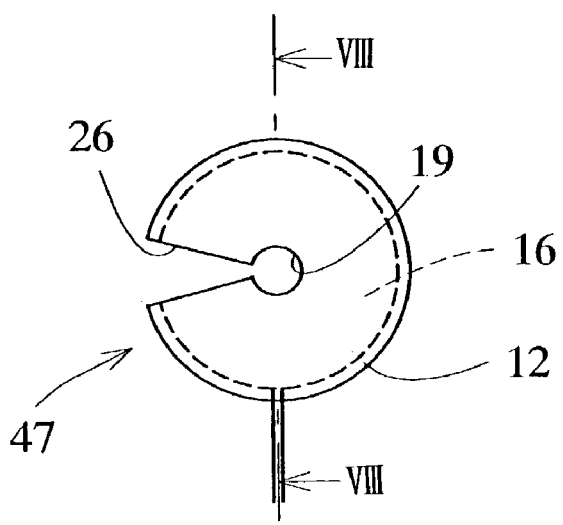
Figure 8:
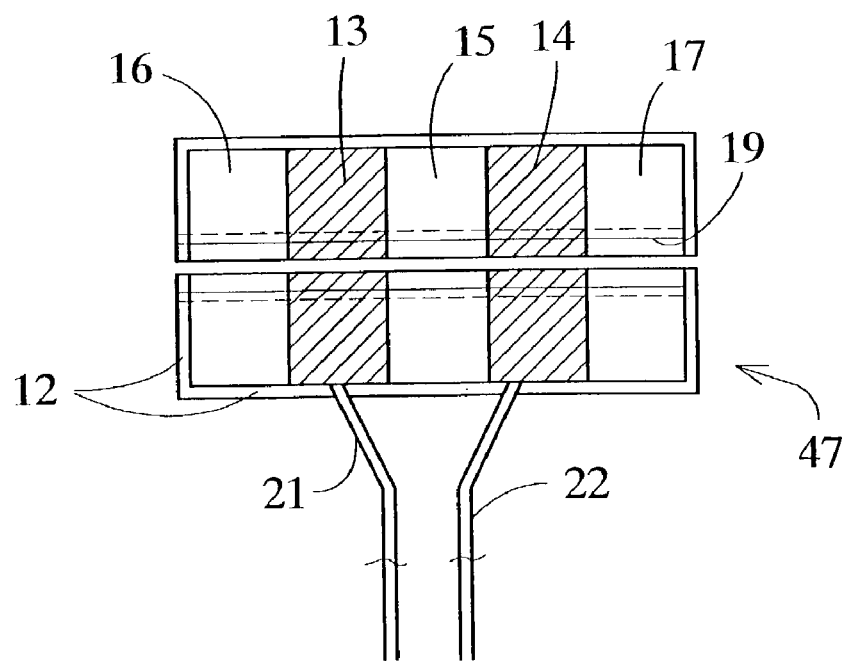
Figure 9:
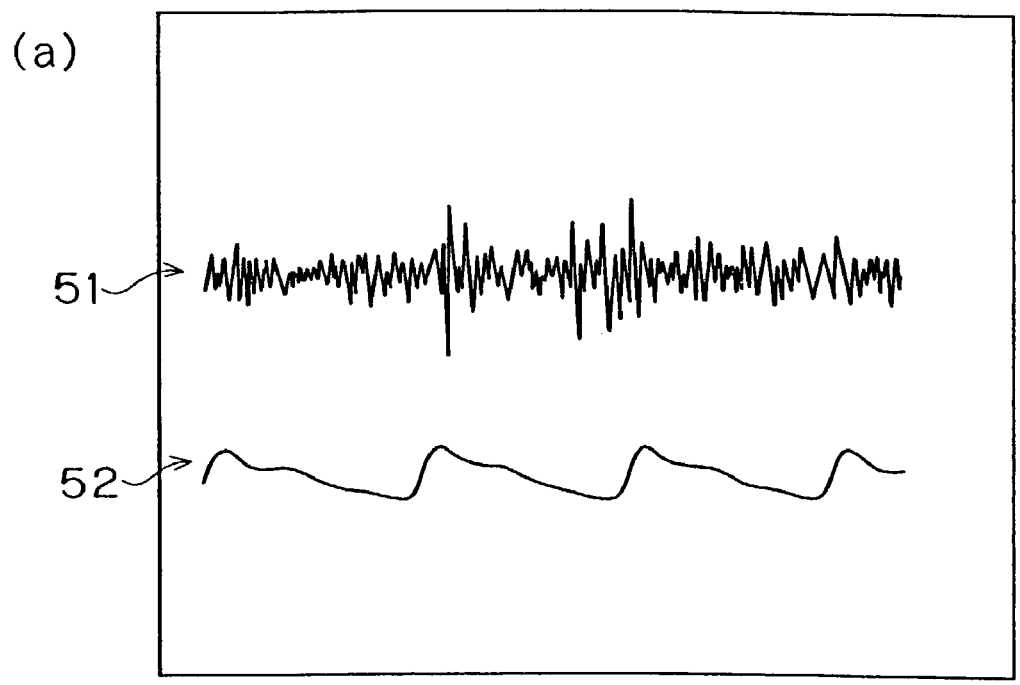
Figure 9:
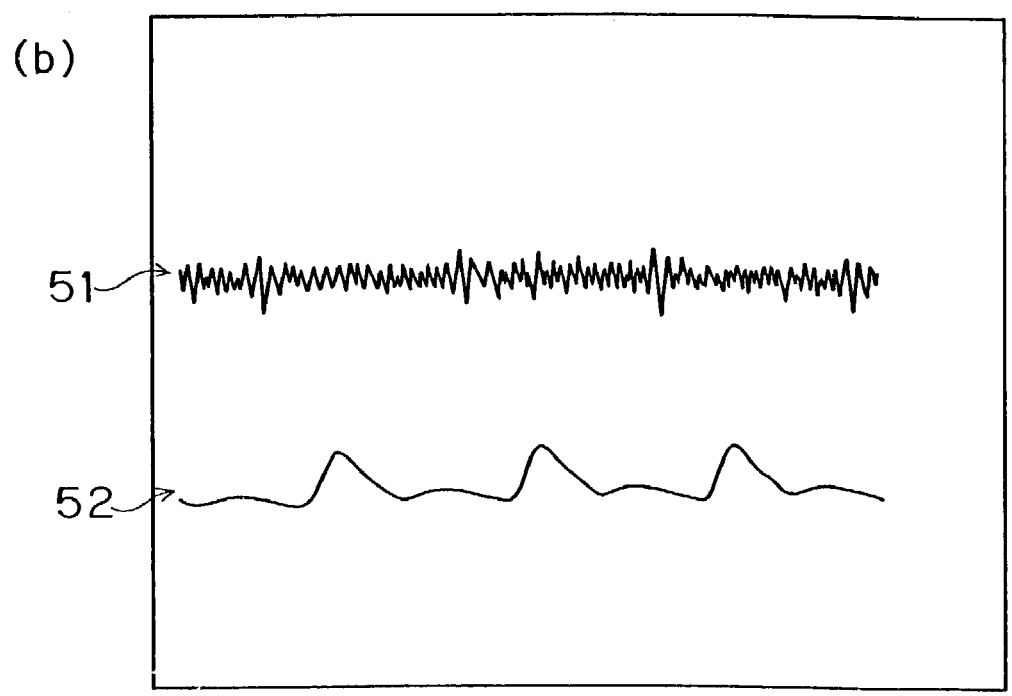

FIGS. 7a, 7b, and 7c are side views of the other embodiment of the in-vivo electrode of this invention respectively;

FIG. 8a is a side view of the other embodiment of the in-vivo electrode of this invention;

FIG. 8b is a cross sectional view taken along the line VIII—VIII of FIG. 8a;

FIGS. 9a and 9b are oscillo graphs showing the relation between neural activity and arterial blood pressure measured using the in-vivo electrode of this invention respectively.

Figure 10:
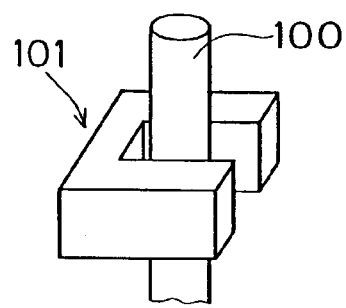
Figure 10:
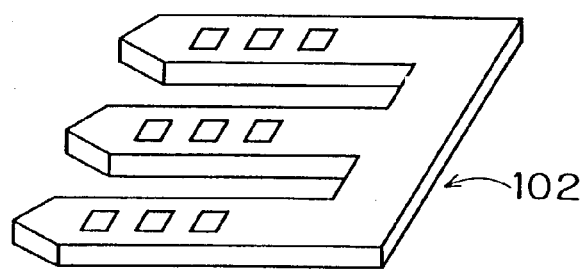
Figure 10:
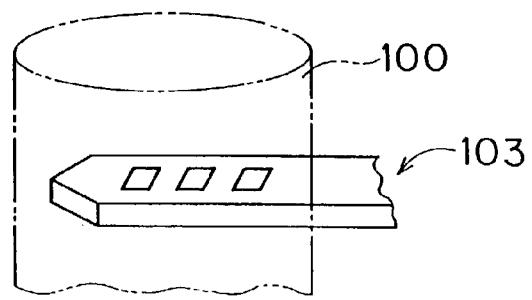

FIGS. 10a, 10b, and 10c are prior art drawings showing a microelectrode and a signal processing electrical circuit assembled in the vicinity of the microelectrode.

Figure 1:
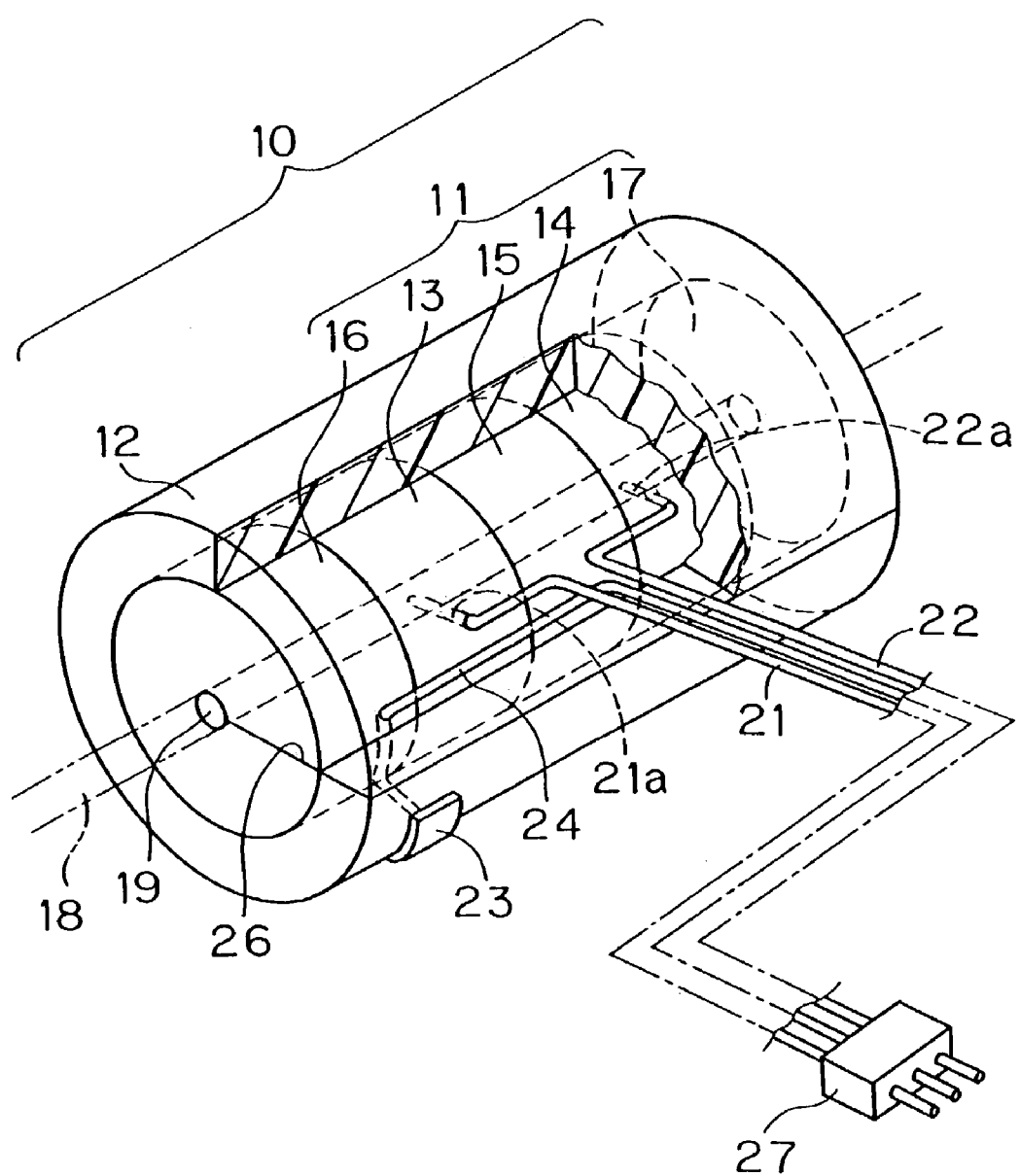
FIG. 1 is a perspective view with a fragmentary sectional view showing an embodiment of the in-vivo electrode of this invention.

The in-vivo electrode 10 shown in FIG. 1 comprises a core body 11 and a cylindrical clad body 12. The core body 11 comprises a pair of cylindrical conductors 13, 14, an intervening member 15 inserted between the conductors, and edge members 16, 17 covering both side ends of each conductor 13, 14. The conductors 13, 14, the intervening member 15, and the edge members 16, 17 have the same diameter with a through-hole 19 to lead a measurement object 18 in each center. The clad body 12, the intervening member 15, and the edge members 16, 17 are made of non-conductive material or insulation material, which is the said insulator of the above. Measuring wires 21, 22 are connected to the conductors 13, 14. Outside of the clad body 12, an earth electrode 23 is provided to which an earth wire 24 is connected. The earth electrode 23 is used as a reference potential (earth potential) by being contacted to an outside anatomy of a measurement object such as neural fascicles etc. Accordingly, in the case that another earth wire is connected to a living body separately, the earth wire 24 is unnecessary and can be abbreviated. In the core body 11 and the clad body 12, a slit 26 reaching the surface from the through-hole 19 is formed.

As the conductors 13, 14, conductive rubber etc. having rubber like elasticity and electrically conductive polymeric material is used. For the intervening member 15 and the edge members 16, 17, silicone rubber etc. having rubber like elasticity and non-conductive polymeric material is preferable. For the conductors 13, 14, the intervening member 15, and the edge members 16, 17, polymeric material such as silicone resins etc. having high adaptability to a living body are preferable in any case. However, other synthetic resin such as polyurethane, nylon elastomer, fluorocarbon resin or rubber are also used. It is preferable to coat the material surface with an antithrombotic drug (heparin, urokinase fixing agent etc.). Further, polymeric material such as biomolecular protein and collagen are used. The outer diameters of these cylindrical members are, for example, about 0.5~1.5 mm, and are preferable to be as small as possible when molding technique allows. The preferred thickness of the conductors 13,14 is 0.4~0.5 mm in which 0.4 mm is more preferable. If the thickness is increased, the range covering the measuring object increases in length to stabilize the measurement. Meanwhile, in the case that a more compact in-vivo electrode is wanted, the thickness is reduced to the limit allowed by the measurement and the molding technique. It is preferred that the thickness of the edge members 16, 17 along its axis be as thin as possible, usually about 0.01 mm~2.0 mm, and specifically about 0.01~0.05 mm. In some cases, the thickness is about 0.05~2.0 mm. Since the thickness of the intervening member 15 along its axis defines the interval of the conductors 13, 14, the interval is determined depending on the measuring object. Usually, it is about 0.4~0.5 mm. The diameter of the through-hole 19 is dependent upon the kind of measuring objects. For example, in the case of sympathetic nerves, it is about 0.15 mm. In addition, depending on the measuring objects such as peripheral nerves etc., it is preferable to make some graded through-holes and in-vivo electrodes and to choose one of them depending on the objects.

For the clad body 12, polymeric material having good adaptability to a living body such as silicone rubber is preferable. The diameter of the clad body 12 is, for example, about 1~2 mm, and the diameter around 1.5 mm is used. The length is usually about 1~3 mm, but it is preferable to decrease the length to be as short as possible if molding technique allows. The slit 26 formed in each conductor 13,14, intervening member 15, and the edge members 16,17 is usually shaped easily in the stage of parts, but it can be shaped also after assembling by taking a scalpel etc. to the members. When a laser beam is used, more machinelike cutting is accomplished. The cutting after assembling saves the labor to align the slit of each part. It is preferred that the slit 26 is made so that it is forced by the elasticity of each cylindrical member in the direction to always close and not to open naturally. Additionally, the conductors 13, 14, the intervening member 15, and the edge members 16, 17 can be assembled previously into the core body 11 by joining with an adhesive. Further, the glad body 12 can be previously adhered to the core body 11.

Figure 2:
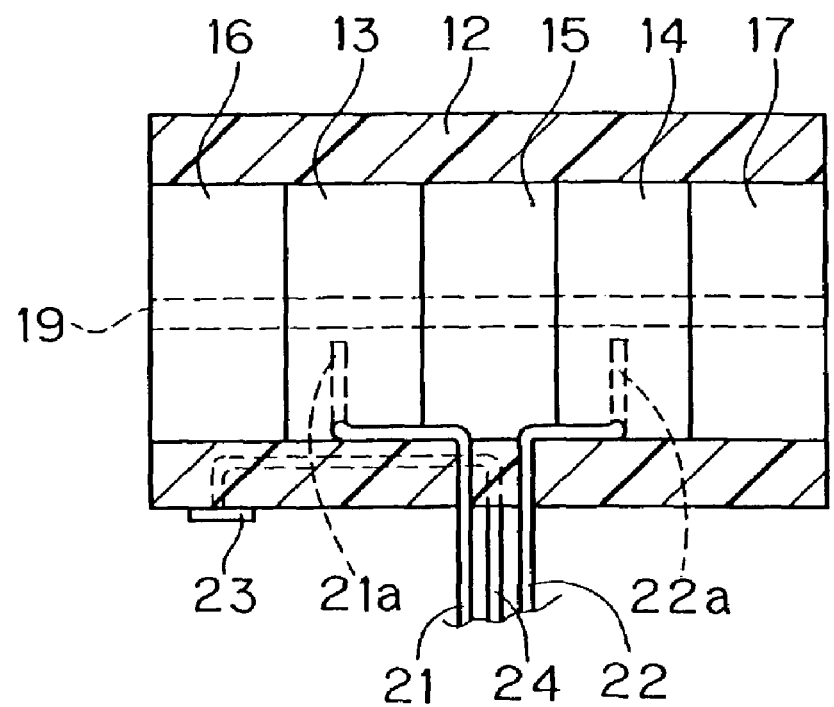
FIG. 2 is a partial sectional view of the in-vivo electrode.
Figure 3:
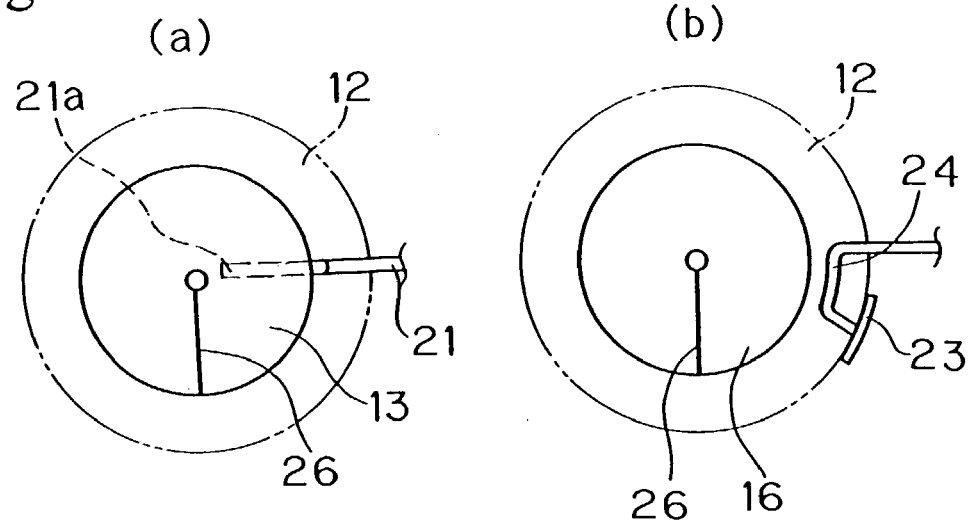
FIG. 3a and FIG. 3b are side views of the conductor and the edge member respectively.

As shown in FIG. 2 and FIG. 3a, one side of the ends 21a, 22a of the measuring wires 21, 22 are embedded into the conductors 13, 14 radially at a depth not reaching the through-hole 19. Further, the other sides of the wires are folded in the direction diametrical parallel and extended to the outside of the conductors. The extended portions are folded along the surface of the conductors 13, 14 in parallel with the axis. The portions are then folded again radially to the outside in the vicinity of the long direction center of the in-vivo electrode 10, and protrude outside through the clad body 12.

One side of the end of the earth wire (See FIG. 3b reference numeral 24) is connected to the earth electrode 23 from the rear side, and then passing through the clad body 12, it is folded radially in the vicinity of the long direction center of the in-vivo electrode, and is extended to the outside. The extended portion of the earth wire 24 is arranged in parallel with the measuring wires 21, 22. These three wires are bundled up with required clearance between them, and are wholly coated with synthetic resin such as polyurethane, nylon, and fluorocarbon resin which have high adaptability to a living body or with silicone rubber, thereby being insulated and reinforced. metal wires having high durability and high adaptability to a living body, for example, a silver wire coated with fluorocarbon resin such as polytetrafluoroethylene (Teflon: Registered trade mark owned by DuPont Co. U.S.A) etc. are preferably used as the measuring wires 21, 22 and the earth wire 24. However, a stainless wire coated with enamel or coated with cashew nut resin, or a nichrome wire can also be used. The diameter of each wire is preferably less than 0.1 mm. For example, in the case of a stainless wire, about 0.05 mm is preferred. A terminal pin 27 for IC (See FIG. 1) is connected to the other end of the three wires. It is preferred that the terminal pin 27 is connected to an in-vivo telemeter so that the multi channel sympathetic nerves neural activity group can be remotely measured.

Figure 4:
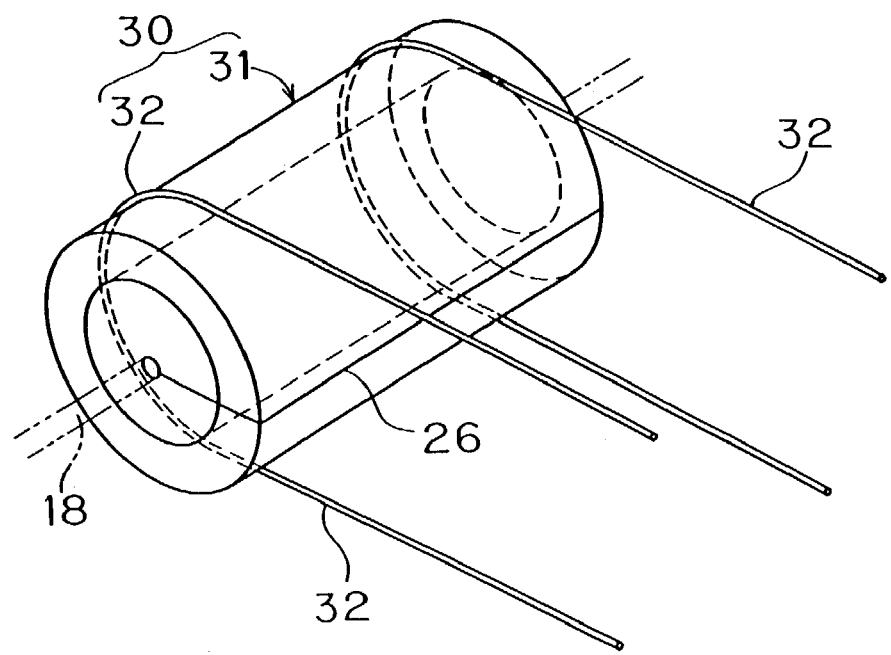
FIG. 4 is a perspective view of the other embodiment of the in-vivo electrode.
Figure 5:
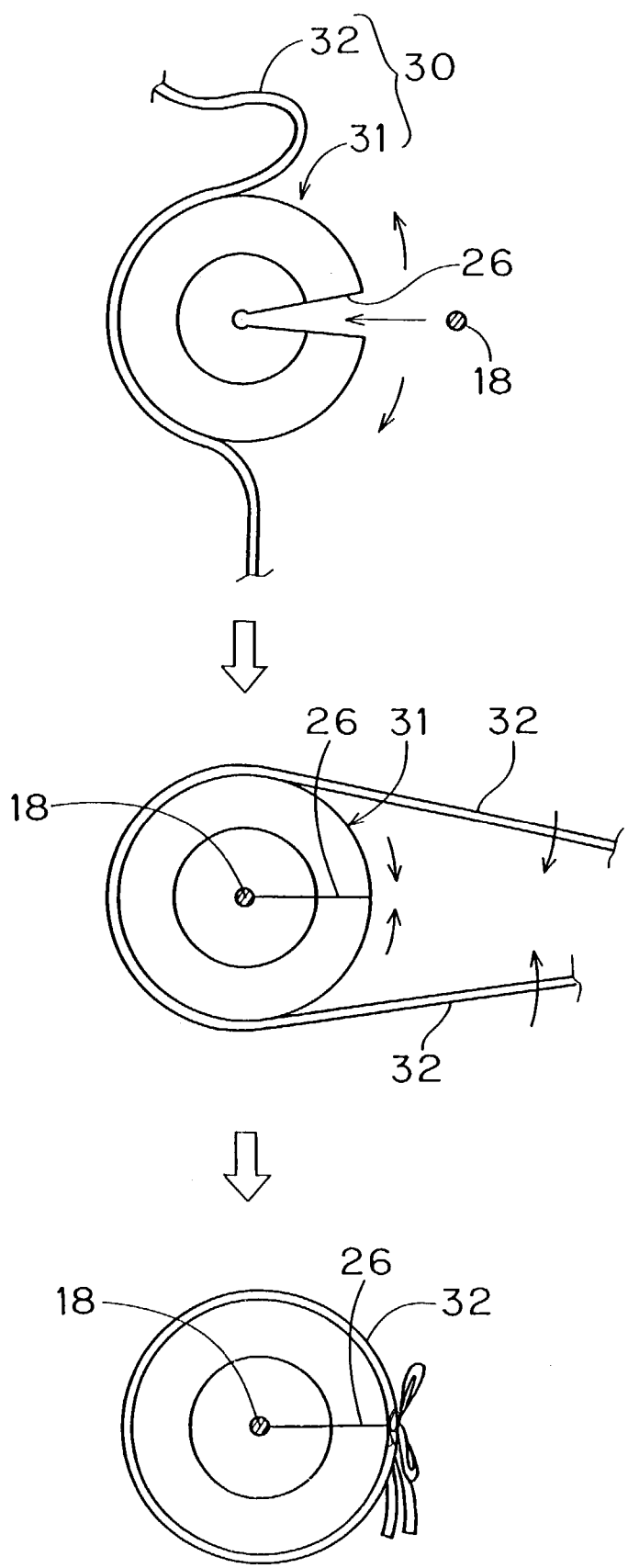
FIG. 5 is a process drawing showing the process of use of the in-vivo electrode of FIG. 2.

The in-vivo electrode 30, shown in FIG. 4, comprises a main body 31 substantially the same as the in-vivo electrode shown in FIG. 1 with a bilateral pair of textile thread 32 adhered to the portion opposite to the slit 26 of the main body. It is preferred that the textile threads 32 are silken threads etc. having high adaptability to a living body. These textile threads 32 are, as shown in FIG. 5, used to fasten the main body 31 after the measuring object, such as a nerve fascicle etc., is led into the through-hole 19 in the condition where the slit 26 of the main body 31 is opened. After that, the slit 26 is closed securely by interknoting both ends of the thread. Thus, contact of the mating faces separated by the slit 26 is strengthened preventing leakage of the body fluid through the slit and enabling long term insulation performance against the outside. Thus far, elastic material for the conductor and insulator were shown as an embodiment but flexible materials can also been used. Especially, when the slit is secured by a thread, the setting of the in-vivo electrode will be eased.

Figure 6:
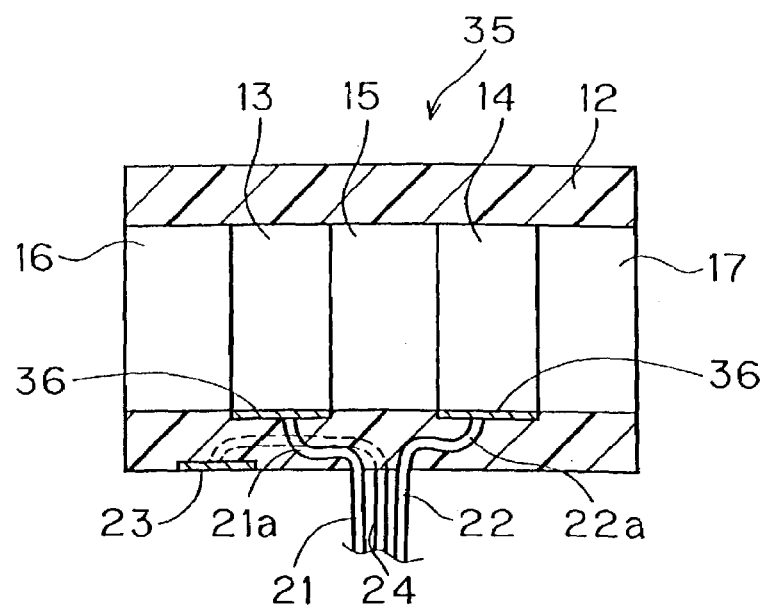
FIG. 6 is a partial sectional view of the other embodiment of the in-vivo electrode of this invention.

In the in-vivo electrode 35 shown in FIG. 6, electrode plates 36 made of conductive resin etc. are embedded inside the surface of the clad body 12 to which the conductors 13, 14 contact. One side of the ends 21a, 22a of the wires 21, 22 are connected to these electrode plates 36. This embodiment has a merit of eliminating the process of embedding the wires in the conductors 13, 14 thereby facilitating easy manufacturing. Further, it facilitates easy assembly by enabling the conductors 13, 14 etc. to be inserted from the edge of the clad body 12.

In the in-vivo electrode 40 shown in FIG. 7a, the slit 26 formed in the conductors 13 etc. is extended to the other side over the through-hole 19. This embodiment has merit in that it allows the slit 26 to open wide. Meanwhile, in the case shown in FIG. 5, the slit 26 ens at the through-hole 19 and the measuring object 18 stops at the position of the through-hole 19, thereby easing the positioning of the object.

In the in-vivo electrode 42 shown in FIG. 7b, the inner diameter d1 of the clad body 12 is smaller than the outer diameter of the core body 11 in its natural state. Therefore, when the clad body 12 is attached to the core body 11, a restoring force due to elasticity works strongly to make the contact of the mating face separated by the slit tighter. But a larger force becomes necessary to open the slit 26 like the electrode shown in FIG. 5.

In the in-vivo electrode 44 shown in FIG. 7c, the core body 11 and the clad body 12 are divided into two sections: half bodies 45, 46 and thread 32 is provided to join them. This embodiment facilitates easy fitting to the nerves etc. But there is a possibility of losing the removed half bodies of the clad body 12 and the core body 11.

In the in-vivo electrode 47 shown in FIG. 8a, the slit 26 opens in its natural state. This embodiment saves the labor of having to open the slit when the nerves etc. are led into the through-hole 19 and facilitates easy handling. The in-vivo electrode 47 is usable in the same procedure as shown in FIG. 5 after inserting the nerves etc. in to the through-hole 19. Additionally, in this in-vivo electrode, the thickness of the clad body 12 is thin and is, therefore soft. Further, the clad body 12 is clad in one united body with the outer surface of the edge member 16, 17, thereby having an advantage that the parts will not easily split from each other. The configuration and the advantage of the other parts are the same as the in-vivo electrode of FIG. 1.

FIG. 9a is an oscillo-graph showing synchronously a neural activity 51 of a renal sympathetic nerve and arterial pressure using the in-vivo electrode of this invention. These continuous measurements allow the investigation of correlation between the neural activity and the blood pressure. Further, FIG. 9b shows the disappearance of neural activity of the renal sympathetic nerve accompanying with the decrease of blood pressure as an effect of the sympathetic nerve blocking treatment (administration of hexamethonium) to an animal under measurement. These results verify that the electrode signals recorded by the electrode of this invention show the neural activity of a sympathetic nerve.

The in-vivo electrode described above can measure the electric discharge in peripheral nerves such as motor nerves, sensory nerves, autonomic nerves (sympathetic nerves and parasympathetic nerves). Further, in addition to nerves, if it is clipped by the through-hole of the in-vivo electrode, the excitatory activity of other anatomies (skeletal muscle and smooth muscle etc.) can be measured and recorded.

In the embodiments described above, any one of the in-vivo electrode is shaped into a cylinder but it can be shaped into a square column. In the case that the electrode is composed by divided sections, in which no flexibility is necessary, rigid materials such as ceramics having good adaptability to a living body can be used. However, in order to protect the anatomy such as nerve etc., the use of polymeric material having flexibility/adaptability is preferable. Additionally, in the embodiments described above, as an anti-noise measure, a pair of difference electrical potentials are recorded using a pair of conductors (bipolar lead), but recording from single pole using one of the electrode wired to a recorder (unipolar lead) can be performed.

What is claimed is:

1. An ultra-miniature in-vivo electrode used for measuring the bioelectrical neural activity, comprising:
   a core body, and
   a cylindrical clad body surrounding the core body,
   wherein the core body and the cylindrical clad body have (1) a center, (2) a through-hole in each center of said core body and said cylindrical clad body said through-hole being aligned in a straight line to lead a measuring objects thru each center of said core body and said cylindrical clad body, and (3) a slit reaching the surface of said core body and said cylindrical clad body from said through-hole,
   wherein the core body comprises a pair of cylindrical conductors, an intervening member inserted between the conductors, an edge member covering each side ends of each conductor, and a pair of wires connected to each said conductor, penetrating said cylindrical clad body to its outside where a surface of said wires are insulated,
   wherein the conductors, the intervening member, and the edge members have the same diameter, and
   wherein the clad body, the intervening member, and the edge member are made of insulating material.

2. An in-vivo electrode according to claim 1, wherein said conductors, said clad body, said intervening member, and said edge member are made of a elastic body, and said slit extends from said through-hole to the outside surface for guiding said measuring object into said through-hole.

3. An in-vivo electrode according to claim 2, wherein said slit is always closed by a elastic force.

4. An in-vivo electrode according to claim 2, wherein said slit stays open by a elastic force.

5. An in-vivo electrode according to claim 2, further comprising a thread binding a periphery of said clad body to keep said slit closed.

6. An in-vivo electrode according to claim 1, further comprising an earth electrode laid on the surface of said clad body, and an earth wire connected to said earth electrode, wherein a surface of said earth wire is insulated.

7. An in-vivo electrode according to claim 1, wherein said cylindrical clad body surrounds the whole periphery of said cylindrical conductors, said intervening member, and said edge member.

8. An in-vivo electrode according to claim 1, wherein said pair of wires is configured to measure the electric potential difference of a nerve fascicle.

* * * * *